United States Patent [19]

Singleton et al.

[11] Patent Number: 5,849,960
[45] Date of Patent: Dec. 15, 1998

[54] HIGHLY BRANCHED PRIMARY ALCOHOL COMPOSITIONS, AND BIODEGRADABLE DETERGENTS MADE THEREFROM

[75] Inventors: David M. Singleton; Louis Kravetz; Brendan Dermot Murray, all of Houston, Tex.

[73] Assignee: Shell Oil Company, Houston, Tex.

[21] Appl. No.: 755,843

[22] Filed: Nov. 26, 1996

[51] Int. Cl.[6] ............................................. C07C 27/20
[52] U.S. Cl. ..................... 568/909; 585/512; 752/182.11
[58] Field of Search .......................... 568/909; 585/512; 252/182.11

[56] References Cited

U.S. PATENT DOCUMENTS

| | | | |
|---|---|---|---|
| 2,654,772 | 10/1953 | Pavlic | 260/459 |
| 2,655,255 | 8/1953 | Brown | 206/4 |
| 2,655,525 | 10/1953 | Banes et al. | 260/459 |
| 2,852,563 | 9/1958 | Hagemeyer et al. | 260/601 |
| 3,119,876 | 1/1964 | Jaros et al. | 260/604 |
| 3,127,451 | 3/1964 | Berkeley, Jr. et al. | 260/638 |
| 3,172,451 | 3/1965 | Leonard | 72/10 |
| 3,231,621 | 1/1966 | Slaugh | 260/604 |
| 3,239,566 | 3/1966 | Slaugh et al. | 260/604 |
| 3,239,569 | 3/1966 | Slaugh et al. | 260/632 |
| 3,239,570 | 3/1966 | Slaugh et al. | 260/632 |
| 3,239,571 | 3/1966 | Slaugh et al. | 260/632 |
| 3,420,898 | 1/1969 | Van Winkle et al. | 260/632 |
| 3,424,815 | 1/1969 | Cannell et al. | 260/683.15 |
| 3,440,291 | 4/1969 | Van Winkle et al. | 260/632 |
| 3,448,157 | 6/1969 | Slaugh et al. | 260/604 |
| 3,448,158 | 6/1969 | Slaugh et al. | 260/604 |
| 3,496,203 | 2/1970 | Morris et al. | 260/439 |
| 3,496,204 | 2/1970 | Morris et al. | 260/439 |
| 3,501,515 | 3/1970 | Van Winkle et al. | 260/439 |
| 3,527,818 | 9/1970 | Mason et al. | 260/632 |
| 3,636,034 | 1/1972 | Ohsumi et al. | 260/459 |
| 3,843,706 | 10/1974 | Weil et al. | 260/458 |
| 3,931,271 | 1/1976 | Baumann et al. | 260/458 |
| 3,952,068 | 4/1976 | Gipson et al. | 260/632 R |
| 4,032,578 | 6/1977 | Savini | 260/601 R |
| 4,426,542 | 1/1984 | Barker et al. | 568/883 |
| 4,474,678 | 10/1984 | Lutz et al. | 252/174.21 |
| 4,959,491 | 9/1990 | Threlkel | 562/94 |
| 4,992,613 | 2/1991 | Brownscombe et al. | 585/666 |
| 5,026,933 | 6/1991 | Blain et al. | 585/7 |
| 5,112,519 | 5/1992 | Giacobbe et al. | 252/174.21 |
| 5,196,625 | 3/1993 | Threlkel et al. | 585/513 |
| 5,389,277 | 2/1995 | Prieto | 252/99 |
| 5,510,306 | 4/1996 | Murray | 502/64 |

FOREIGN PATENT DOCUMENTS

| | | | |
|---|---|---|---|
| 0329670 | 10/1987 | European Pat. Off. | C07C 69/34 |
| 0300444 | 7/1988 | European Pat. Off. | C07C 141/08 |
| 0373850 | 12/1989 | European Pat. Off. | C11D 3/386 |
| 0439316 | 1/1991 | European Pat. Off. | C11D 1/14 |
| 798541 | 6/1956 | United Kingdom . | |
| 85/02175 | 5/1985 | WIPO | C07C 29/14 |
| WO 95/21225 | 8/1995 | WIPO | C09K 7/00 |
| 97/38956 | 10/1997 | WIPO | C07C 1/04 |
| 97/38957 | 10/1997 | WIPO | C07C 2/06 |
| 97/38972 | 10/1997 | WIPO | C07C 303/24 |
| 97/39087 | 10/1997 | WIPO | C11D 1/14 |
| 97/39088 | 10/1997 | WIPO | C11D 1/14 |
| 97/39089 | 10/1997 | WIPO | C11D 1/14 |
| 97/39090 | 10/1997 | WIPO | C11D 1/14 |
| 97/39091 | 10/1997 | WIPO | C11D 1/14 |

OTHER PUBLICATIONS

"Atlas of Zeolite Structure Types" by W. M. Meier and D. H. Olson, published on behalf of the Structure Commission of the International Zeolite Association, May 24, 1989, pp. 4–10, 134–135, 106–107, and 64–65.

*Primary Examiner*—John Kight
*Assistant Examiner*—Raymond Covington
*Attorney, Agent, or Firm*—Dennis V. Carmen

[57] ABSTRACT

There is provided a new branched primary alcohol composition and the sulfates thereof exhibiting good cold water detergency and biodegradability. The branched primary alcohol composition has an average number of branches per chain of at least 0.7, having at least 8 carbon atoms and contianing both methyl and ethyl branches. The primary alcohol composition may also contain less than 0.5 atom % of quaternary carbon atoms, and a significant number ethyl branches, terminal isopropyl branches, and branching it the $C_3$ position relative to the hydroxyl carbon. The process for its manufacture is by skeletally isomerizing an olefin feed having at least 7 carbon atoms followed by conversion to an alcohol, as by way of hydroformylation, and ultimately, sulfation to obtain a detergent surfactant. Useful catalysts include the zeolites having at least one channel with a crystallographic free diameter along the x and/or y planes of the [001] view ranging from greater than 4.2 Å and less than 7 Å, but allows one to skeletally isomerize the olefin to produce a variety of branches, while retaining ready biodegradability and good cold water detergency.

39 Claims, No Drawings

HIGHLY BRANCHED PRIMARY ALCOHOL COMPOSITIONS, AND BIODEGRADABLE DETERGENTS MADE THEREFROM

1. FIELD OF THE INVENTION

The invention pertains to a new primary alcohol composition and the sulfates thereof simultaneously exhibiting improved cold water detergency and ready biodegradability. In particular, the invention relates to a branched primary alcohol composition having an average number of branches of at least 0.7, a carbon chain length of at least 8 carbons, and having methyl and ethyl branches, as well as to a skeletally isomerized primary alcohol composition and a process for its manufacture by skeletally isomerizing an olefin followed by a hydroformylation, and where a detergent is desired, sulfation.

2. BACKGROUND OF THE INVENTION

The alcohols of long chain olefins having about 10 to 28 carbon atoms have considerable commercial importance in a variety of applications, including detergents, soaps, surfactants, and freeze point depressants in lubricating oils. These alcohols are produced by any one of commercial processes, such as the oxo or hydroformylation of long chain olefins. Typical long chain alcohols are the commercially available NEODOL® alcohols made by Shell Chemical Company, the EXXAL® alcohols available from Exxon Chemical, and the LIAL® alcohols available from Enichem.

In the manufacture of the NEODOL® alcohols, a predominantly linear olefin feed is subjected to hydroformylation by reacting carbon monoxide and hydrogen onto the olefin in the presence of an Oxo catalyst to form an alcohol. In excess of 80% of the number of alcohol molecules in the resultant alcohol composition are linear primary alcohols. Of the branched primary alcohols in the composition, substantially all, if not all, of the branching is on the $C_2$ carbon atom relative to the hydroxyl bearing carbon atom. These alcohols can subsequently be converted to anionic or non-ionic detergents or general surfactants by sulfonation or ethoxylation, respectively, of the alcohol. Also known as anionic surfactants for detergents are the alcohol-ethoxysulfates.

The NEODOL® line of alcohols has met with considerable commercial success with detergents because the NEODOL® alcohol compositions can be economically produced with high yields of linear alcohols. The desire to use linear alcohols as intermediates for detergent grade surfactants exists because it is generally recognized that linear alcohols biodegrade, while the branched long chain alcohol sulfonates exhibit poor biodegradability. Since detergents and soaps used by consumers for washing are ultimately released into the environment, the need to provide a surfactant or detergent which biodegrades is well recognized.

For example, U.S. Pat. No. 5,112,519 describes the manufacture of a surfactant by oligomerizing $C_3$ and $C_4$ olefins through a surface deactivated ZSM-23 catalyst to form oligomers, hydroformylating the oligomer, and recovering a semi-linear alcohol composition having less than 1.4 methyl branches, and whose branching is limited to methyl branches. The alcohol can be ethoxylated and/or sulfated and is reported to be biodegradable, and further have improved low temperature properties compared to isotridecyl alcohol. Retaining the linearity of the alcohol composition to less than 1.4, along with obtaining methyl branching were important considerations to achieving a biodegradable surfactant. It would be desirable, however, to obtain a biodegradable surfactant without limiting the branching to methyl branches, without limiting the branching to under 1.4, and without limiting oneself to a ZSM 23 surface deactivated catalyst. It would also be desirable to make a biodegradable surfactant without conducting oligomerization reactions through zeolite catalysts, which are expensive and may coke up or be used up quickly if one needs to build chain length through the catalyst.

Another product, EXXAL® 13, is derived from propylene oligomerization through acid catalysis to a wide range of mono-olefins, the range having an average of C13s being distilled out, but containing some olefins in the $C_{10-15}$ range. The olefin is then subjected to hydroformylation using an oxo process. EXXAL® 13 is reported to be a 3–4 methyl branched tridecyl-alcohol known for its use in lubricants and in those detergent formulations which do not require rapid biodegradation. This is because EXXAL® 13 only slowly biodegrades. While such a high amount of branching is not necessary, it would be desirable to make a surfactant having a higher amount of branching for detergency which is nevertheless readily biodegradable.

U.S. Pat. No. 5,196,625 describes a dimerization process for producing linear and/or mono-branched C10 to C28 olefins using dimerization catalysts, for the production of biodegradable alkylbenzene sulfonates detergents by alkylating the olefins onto benzene. No mention is made of using the dimerized olefins to make alcohols. Further, the patentee reported that it is generally recognized that "linear and mono-branched alkyl aromatic sulfonates are generally much more readily biodegraded than multibranched alkyl aromatic sulfonates and, hence, much more desirable as detergents." For this reason, the patentee sought to ensure that the olefins made were substantially linear and mono-branched. Again, it would be desirable to make highly branched products that have good detergency and biodegradability from alcohols, and also without regard to limitations on the amount of branching being low.

The patentee of U.S. Pat. No. 4,670,606 likewise recommended using "linear detergent oxo-alcohols or those in which the linear fraction is as high as possible" for biodegradability reasons in the detergent field, while oxo-alcohols that are highly branched are desirable as lubricating oil additives because the branching depresses the freezing point of the lubrication oil. Thus, the invention was directed towards methods to separate the two from a mixture.

The desire to make highly linear high olefin alcohols was also expressed in U.S. Pat. No. 5,488,174. In discussing the problems encountered by cobalt carbonyl catalyzed hydroformylation of olefins, the patentee noted that this process produced a composition which contained branched compounds when starting with internal olefins, which was particularly undesirable because of its poor biodegradability. Thus, the patentee recommended using catalytic processes which would produce mixtures exhibiting high linear/branching ratios.

As previously noted, the highly linear NEODOL® alcohol line of intermediates for the production of detergent surfactants are commercially successful, in part, because of their high linearity rendering them readily biodegradable. However, the high degree of linearity also increased the hydrophobicity of the hydrophobe part of the chain, thereby decreasing its cold water solubility/detergency. In general, the highly linear alcohol sulfates suffer from poor cold water solubility/detergency. Along with the concern for using biodegradable compounds, government regulations are also calling for the lowering of wash temperatures.

Thus, there exists a growing need to find alcohol intermediates which are both biodegradable and exhibit good detergency at cold wash temperatures. The solution to this problem was not merely as simple as increasing the branching of the higher olefin in alcohol in order to decrease hydrophobicity and thereby hopefully increase cold water detergency, because, as noted above, it is well recognized that branched compounds exhibit poor biodegradability.

3. SUMMARY OF THE INVENTION

We have discovered a new composition of primary alcohols, their sulfate derivatives, and processes for making, which sulfates simultaneously satisfy requirements for biodegradability and cold water detergency. There is now provided a primary alcohol sulfate composition obtained by sulfating an alkyl branched primary alcohol composition having at least 8 carbon atoms, wherein the alcohol composition has an average number of branches per molecule chain of at least 0.7, containing not only methyl branches but also ethyl branches.

We have also discovered a branched primary alcohol composition having at least 8 carbon atoms, an average number of branches per chain of at least 0.7, and having less than 0.5 atom % of quaternary carbon atoms, also containing at least methyl and ethyl branching.

The invention is also be characterized as a branched primary alcohol composition comprising skeletally isomerized olefins converted to primary alcohols. A skeletally isomerized hydrophobe means that the hydrophobe, which was an olefin, was subjected to conditions which branched the hydrophobe such that the number of carbon atoms in the olefin prior to and subsequent to the isomerization condition is substantially the same. This may be distinguished from branching occurring by oligomerizing small chain length olefins to larger chain length olefin where a zeolite catalyst is used to both build chain length and add branching.

A significant number of alkyl branches are located on the $C_3$ atoms of the alcohol composition, and a significant number of the total branching on the alchohol molecules are methyl and ethyl branches. Many of the primary alcohol composition molecules are isopropyl terminated. As a preferred embodiment, the average number of branches ranges from 1.5 to 2.3. Each of these primary alcohol compositions can be sulfated to provide surfactant compositions which exhibit good cold water detergency and biodegradability.

Other preferred and more detailed characteristics of the new structures are described further herein.

Additional steps toward forming the sulfate are sulfating the branched primary alcohol compositions using methods described below. There is further provided cleaning and washing compositions, particularly detergents, employing the sulfates of the invention, described in more detail below.

There is also provided a method for making a saturated branched primary alcohol composition having carbon atoms in the range of 8 to 36 carbon atoms and an average number of branches per molecule chain, which comprises:
 a) contacting a feed comprising linear olefins having 7 to 35 carbon atoms with a catalyst effective for skeletally isomerizing said linear olefin to yield a skeletally isomerized olefin; and
 b) converting the skeletally isomerized olefin to form a saturated branched primary alcohol, preferably by hydroformylation.

The skeletal isomerization process for making the primary alcohol composition of the invention preferably uses a zeolite having at least one channel with a crystallographic free diameter ranging from greater than 4.2 Å and less than 7 Å. The catalyst preferably has an elliptical pore size large enough to permit entry of a linear olefin and diffusion, at least partially, of a methyl branched isoolefin and small enough to retard coke formation. More specifics concerning types of suitable and preferable catalysts are explained in detail below.

The process avoids the need for using a zeolite to both oligomerize and branch. One also has the advantage of being able to use commercially available high chain length olefins, i.e. $C_8$ and longer, which might not have much use or is in excess, and branch the olefins followed by hydroformylation and sulfation to provide a detergent having excellent detergency and biodegradability. This process also does not restrict the types of branching to only methyl branches, but allows one to skeletally isomerize the olefin to produce a variety of branches, while retaining ready biodegradability and good cold water detergency

4. DETAILED DESCRIPTION OF THE INVENTION

As used herein, the phrase average number of branches per molecule chain refers to the average number of branches per alcohol molecule, as measured by $^{13}C$ Nuclear Magnetic Resonance ($^{13}C$ NMR ) as discussed below. The average number of carbon atoms in the chain are determined by gas chromatography.

Various references will be made throughout this specification and the claims to the percentage of branching at a given carbon position, the percentage of branching based on types of branches, average number of branches, and percentage of quaternary atoms. These amounts are to be measured and determined by using a combination of the following three $^{13}C$-NMR techniques. (1) The first is the standard inverse gated technique using a 45-degree tip $^{13}C$ pulse and 10 s recycle delay (an organic free radical relaxation agent is added to the solution of the branched alcohol in deuterated chloroform to ensure quantitative results). (2) The second is a J-Modulated Spin Echo NMR technique (JMSE) using a 1/J delay of 8 ms (J is the 125 Hz coupling constant between carbon and proton for these aliphatic alcohols). This sequence distinguishes carbons with an odd number of protons from those bearing an even number of protons, i.e. $CH_3$/CH vs $CH_2/C_q$($C_q$ refers to a quaternary carbon). (3) The third is the JMSE NMR "quat-only" technique using a 1/2J delay of 4 ms which yields a spectrum that contains signals from quaternary carbons only. The JSME NMR quat only technique for detecting quaternary carbon atoms is sensitive enough to detect the presence of as little at 0.3 atom % of quaternary carbon atoms. As an optional futher step, if one desires to confirm a conclusion reached from the results of a quat only JSME NMR spectrum, one may also run a DEPT-135 NMR sequence. We have found that the DEPT-135 NMR sequence is very helpful in differentiating true quaternary carbons from breakthrough protonated carbons. This is due to the fact that the DEPT-135 sequence produces the "opposite" spectrum to that of the JMSE "quat-only" experiment. Whereas the latter nulls all signals except for quaternary carbons, the DEPT-135 nulls exclusively quaternary carbons. The combination of the two spectra is therefore very useful in spotting non quaternary carbons in the JMSE "quat-only" spectrum. When referring to the presence or absence of quaternary carbon atoms throughout this specification, however, we mean that the given amount or absence of the quaternary carbon is as measured by the quat only JSME NMR method. If one optionally desires to confirm the results, then also using the DEPT-135 technique to confirm the presence and amount of a quaternary carbon.

The detergency evaluations conducted and as used throughout were based from a standard high density laundry powder (HDLP) Detergency/Soil Redeposition Performance test. The evaluations in the working examples were conducted using Shell Chemical Company's radiotracer techniques at the designated temperatures in Table III at a water hardness of 150 ppm as $CaCO_3$ ($CaCl_2$/$MgCl_2$ =3/2 on a molar basis). The primary alcohol sulfated compositions of the invention were tested, on a ¼ cup basis, against multisebum, cetanesqualane and clay soiled permanent press 65/35 polyester/cotton (PPPE/C) fabric. The HDLP's were tested at 0.74 g/l concentration, containing 27 wt % of the primary alcohol sulfate composition, 46 wt % of builder (zeolite-4A), and 27 wt % of sodium carbonate.

The composition of the radiolabeled Multisebum Soil was as follows:

| Component | Label | % wt. |
|---|---|---|
| Cetane | 3H | 12.5 |
| Squalane | 3H | 12.5 |
| Trisearin | 3H | 10 |
| Arachis (Peanut) Oil | 3H | 20 |
| Cholesterol | 14C | 7 |
| Octadecanol | 14C | 8.0 |
| Oleic Acid | 14C | 15.0 |
| Stearic Acid | 14C | 15.0 |

A Terg-O-Tometer was used to wash the swatches at 15 minute intervals. The wash conditions were set to measure both cold water detergency at 50° F. and warm water detergency at 90° F. The agitation speed was 100 rpm. Once the 4"×4" radiotracer soiled swatches were washed by the Terg-O-Tometer, they were hand rinsed. The wash and rinse waters were combined for counting to measure sebum soil removal. The swatches were counted to measure clay removal.

For details concerning the detergency methods and radiotracer techniques, reference may be had to B. E. Gordon, H. Roddewig and W. T. Shebs, HAOCS, 44:289 (1967), W. T. Shebs and B. E. Gordon, JAOCS, 45:377 (1968), and W. T. Shebs, Radioisotope Techniques in Detergency, Chapter 3, Marcel Dekker, New York (1987), each incorporated herein by reference.

The biodegradation testing methods for measuring the biodegradability of the working example sulfates were conducted in accordance with the test methods established in 40 CFR §796.3200, also known as the OECD 301D test method, incorporated herein by reference. By a biodegradable primary alcohol sulfate composition or surfactant is meant that that the compound or composition gives a measured biochemical oxygen demand (BOD) of 60% or more within 28 days, and this level must be reached within 10 days of biodegradation exceeding 10 percent.

The primary alcohol composition of the invention contains an average chain length per molecule of at least 8, preferably ranging from 8–36 carbon atoms. For many surfactant applications, such as detergents, the alcohol composition contains an average carbon chain length of 11, 12, 13, 14, 15, 16, 17, 18, or 19 carbon atoms, or any decimal inbetween, expressed as an average within the range of 11 to 19 carbon atoms. The number of carbon atoms includes carbon atoms along the chain backbone as well as branching carbons.

Preferably, at least 75 wt %, more preferably, at least 90 wt. % of the molecules in the primary alcohol composition have chain lengths ranging from 11 to 19 carbon atoms. As one feature of the invention, the average number of branches is at least 0.7, as defined and determined above. While there is no particular upper limit to the average number of branches per molecule, those having an average number of branches of at least 1.5, in particular ranging from 1.5 to about 2.3, especially from 1.7 to 2.1, achieve a good balance of cold water detergency and biodegradability when sulfated. Conventional linear alcohol sulfates contain an average number of branches of only 0.05 to 0.4, and are quite biodegradable. Up to this point, however, the introduction of a higher degree of branching for the purpose of improving cold water detergency has lead to failures in biodegradability tests. The primary alcohol composition of the invention, when sulfated, has the advantage of introducing a large number of branches to improve its cold water properties without sacrificing biodegradability. The cold water properties are improved when the amount of branching is at least 1.5.

A second feature of the invention lies in the provision of a primary alcohol composition having at least 8 carbon atoms, an average number of branches per molecule chain of at least 0.7, and less than 0.5 atom % of $C_q$'s as measured by a quat only JMSE modified $_{13}$C-NMR having a detection limit of 0.3 atom % or better, and preferably an primary alcohol composition which contains no $C_q$'s as measured by this NMR technique. For reasons not yet clearly understood, it is believed that the presence of $C_q$'s on an alcohol molecule prevents the biodegradation of that particular sulfated molecule by biological organisms. Alcohols containing as little as 1 atom % of $C_q$'s have been been found to biodegrade at failure rates. It is also believed that previous attempts at the introduction of a high degree of branching has led to the formation of a sufficient number of $C_q$'s to account for biodegradation failure.

A third feature of the invention lies in a primary alcohol composition comprising skeletally isomerized olefins converted to primary alcohols.

In a preferred embodiment of the invention, less than 5% of the alcohol molecules in the primary alcohol composition are linear alcohols. The efficient reduction in the number of linear alcohols to such a small amount in the composition results from introducing branching on an olefin feedstock by a skeletal isomerization technique using efficient catalysts as described further below, rather than introducing branching by methods such as acid catalyzed oligomerization of propylene molecules, or zeolite catalyzed oliomerization techniques. In a more preferable embodiment, the primary alcohol composition contains less than 3% of linear alcohols. The percentage of molecules which are linear may be determined by gas chromatography.

In another embodiment of the invention, the primary alcohol composition of the invention may be characterized by the NMR technique as having from 5 to 25% branching on the $C_2$ carbon position, relative to the hydroxyl carbon atom. In a more preferred embodiment, from 10 to 20% of the number of branches are at the $C_2$ position, as determined by the NMR technique.

The primary alcohol composition also generally have from 10% to 50% of the number of branches on the $C_3$ position, more typically from 15% to 30% on the $C_3$ position, also as determined by the NMR technique. When coupled with the number of branches seen at the $C_2$ position, the primary alcohol composition of the invention contain significant amount of branching at the $C_2$ and $C_3$ carbon positions.

Not only do the primary alcohol composition of the invention have a significant number of branches at the $C_2$ and $C_3$ positions, but we have also seen by the NMR technique that many of the primary alcohol compositions have at least 5% of isopropyl terminal type of branching, meaning methyl branches at the second to last carbon position in the backbone relative to the hydroxyl carbon. We have even seen at least 10% of terminal isopropyl types of branches in the primary alcohol composition, typically in the range of 10% to 20%. In typical hydroformylated olefins of the Neodol® series, less than 1%, and usually 0.0%, of the branches are terminal isopropyl branches. By skeletally isomerizing the olefin according to the invention, however, the primary alcohol composition contains a high percentage of terminal isopropyl branches relative to the total number of branches, desirable to improve the cold water solubility of the primary alcohol composition sulfates. The introduction of the isopropyl termination was accomplished without sacrificing the biodegradability of the sulfated primary alcohol composition.

Considering the combined number of branches occurring at the $C_2$, $C_3$, and isopropyl positions, there are embodiments of the invention where at least 20%, more preferably at least 30%, of the branches are concentrated at these positions. The scope of the invention, however, includes branching occurring across the length of the carbon backbone. In another preferred embodiment of the invention, the total number of methyl branches number at least 40%, even at least 50%, of the total number of branches, as measured by the NMR technique described above. This percentage includes the overall number of methyl branches seen by the NMR technique described above within the $C_1$ to the $C_3$ carbon positions relative to the hydroxyl group, and the terminal isopropyl type of methyl branches.

Significantly, we have consistently observed a significant increase in the number of ethyl branches over those seen on Neodol® alcohols. The number of ethyl branches can range from 5% to 30%, most typically from 10% to 20%, based on the overall types of branching that the NMR method detects. Thus, the skeletal isomerization of the olefins produced both methyl and ethyl branches, and these alcohols, when sulfated, worked exceedingly well in biodegradability and detergency tests. Thus, the types of catalysts one may use to perform skeletal isomerization are not restricted to those which will produce only methyl branches. The presence of a variety of branching types is believed to enhance a good overall balance of properties.

The olefins used in the olefin feed for skeletal isomerization are at least $C_7$ mono-olefins. In a preferred range, the olefin feed comprises $C_7$ to $C_{35}$ mono-olefins. Olefins in the $C_{11}$ to $C_{19}$ range are considered most preferred for use in the instant invention, to produce primary alcohol compositions in the $C_{12}$ to $C_{20}$ range, which are the most common ranges for detergent applications. As a general rule, the higher the carbon number of the surfactant derivative, the more noticeable are the improvements in physical properties and formulateability.

In general, the olefins in the olefin feed composition are predominately linear. Attempting to process a predominately branched olefin feed, containing quaternary carbon atoms or extremely high branch lengths, would require separation methods after passing the olefin stream across the catalyst bed to separate these species from the desired branched olefins. While the olefin feed can contain some branched olefins, the olefin feed processed for skeletal isomerization preferably contains greater than about 50 percent, more preferably greater than about 70 percent, and most preferably greater than about 80 mole percent or more of linear olefin molecules.

The olefin feed does not consist of 100% olefins within the specified carbon number range, as such purity is not commercially available. The olefin feed is usually a distribution of mono-olefins having different carbon lengths, with at least 50 wt. % of the olefins being within the stated carbon chain range or digit, however specified. Preferably, the olefin feed will contain greater than 70 wt. %, more preferably about 80 wt. % or more of mono-olefins in a specified carbon number range (e.g., C7 to C9, C10 to C12, C11 to C15, C12 to C13, C15 to C18, etc.), the remainder of the product being olefin of other carbon number or carbon structure, diolefins, paraffins, aromatics, and other impurities resulting from the synthesis process. The location of the double bond is not limited. The olefin feed composition may comprise α-olefins, internal olefins, or a mixture thereof.

Chevron Alpha Olefin product series (trademark of and sold by Chevron Chemical Co.), manufactures predominantly linear olefins by the cracking of paraffin wax. Commercial olefin products manufactured by ethylene oligomerization are marketed in the United States by Shell Chemical Company under the trademark NEODENE and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. Linear internal olefin products in the C8 to C22 range are marketed by Shell Chemical Company and by Liquichemica Company.

The catalyst used to treat the feed of linear olefins is one which is effective for skeletally isomerizing a linear olefin composition into an olefin composition having an average number of branches per molecule chain of at least 0.7. This catalyst contains a zeolite having at least one channel with a crystallographic free channel diameter ranging from greater than 4.2 Å and less than 7 Å, measured at room temperature, with essentially no channel present which has a free channel diameter which is greater than 7 Å.

The catalyst should contain at least one channel having a crystallographic free diameter at the entrance of the channel within the stated range. The catalyst should not have a diameter at the entrance of a channel which exceeds the 7 Å upper limit to the range. Zeolites possessing channel diamters greater than 0.7 nm are susceptible to unwanted aromatization, oligomerization, alkylation, coking and by-product formation. On the other hand, if the zeolite does not contain a channel having a free diameter along either of the x or y planes of greater than 4.2 Å, the channel size becomes too small to allow diffusion of the olefin into and out of the channel pore once the olefin becomes branched. Thus, the zeolite must have at least one channel with free diameters of that channel within the range of greater than 4.2 Å and less than 7 Å. All other specifications are preferences.

Without being bound to a theory, it is believed that the olefin molecule, due to its high carbon chain length, does not have to enter into the zeolite channel, diffuse through, and exit the other end of the channel. The rate of branching seen when passing the olefin feed across the zeolite does not correspond to the theoretical rate of branching if each olefin molecule were to pass through the channels. Rather, it is believed that most of the olefins partially penetrate the channel for a distance effective to branch the portion of the chain within the channel, and subsequently withdraw from the channel once isomerized. In this case, the olefin molecules in the composition would predominately have a structure which is branched at the ends of the olefin carbon backbone, and substantially linear towards the center of the molecule, i.e., at least 25% of the carbons at the center are unbranched. The scope of the invention, however, includes branching anywhere along the carbon backbone within the parameters described above with respect to the molecular structure.

Preferred embodiments of the zeolite structure are described in U.S. Pat. No. 5,510,306, the fill contents of which are incorporated herein by reference. Zeolite structures are also described in the Atlas of Zeolite Structure Types, by W. M. Meier and D. H. Olson, incorporated herein by reference. With respect to structure, in a preferred embodiment, the catalyst contains a channel having free diameters within the range of greater than 4.2 Å to less than 7 Å along both the x and y planes in the [001] view. Zeolites with this specified channel size are typically referred to as medium or intermediate channel zeolites and typically have a 10-Tmember (or puckered 12-Tmember) ring channel structure in one view and a 9-Tmember or less (small pore) in another view, if any. There is no limit to the number of channels or their orientation (parallel, non-interconnecting intersections, or interconnecting at any angle) in the zeolite. There is also no limit to the size of the channels which are outside of the stated range in both the x and y planes, so long as these other channels do not have free diameter in either of the x or y planes which is greater than 7 Å. For example, other channels having a free diameter of 4.2 or less in one or both of the x or y are within the scope of the invention.

There is also no limit on the number of dimensions, one, two, or three, that the channel system may have. While the scope of the invention includes two or three dimensional zeolites with interconnecting channels having any size less than 7 Å, and including at least one channel within the stated range, there may exist limited circumstances where, for example, α-olefins may meet at the intersection of the interconnecting channels and dimerize or oligomerize, depending on the size of the olefin, the proximity of the interconnecting intersection to the channel entrances, the size of the interconnecting intersection, temperature, flow rates, among other factors. While it is unlikely that such dimer could diffuse back out of the zeolite, the dimer may coke the catalyst or crack within the channel structure, forming by-product olefins having quaternary carbon branching. Thus, the interconnecting channel system in a two or three dimensional zeolite should have free diameters effective to prevent the formation of dimers, trimers, or oligomers under the given processing conditions, which when cracked, can produce quaternary branched by-products. In a preferred embodiment, all channels interconnecting to the channel within the stated range have free diameters in both of the x and y planes of 4.2 Å or less in order to eliminate the possibility that two olefin molecules would contact each other within the zeolite and dimerize or trimerize. This preference, however, applies only to interconnecting channels. A zeolite containing more than one channel, whether one, two, or three dimensional or even intersecting on different planes, but none of which interconnect, does not raise the possibility of dimerization or trimerization because the channels do not connect. Thus, there is no preference for these types of structures, so long as the basic requirements noted above are observed.

Examples of zeolites, including molecular sieves, that can be used in the processes of this invention with a channel size between about 0.42 nm and 0.7 nm, include ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4A, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite. The isotypic structures of these frameworks, known under other names, are considered to be equivalent. An overview describing the framework compositions of many of these zeolites is provided in New Developments in Zeolite Science Technology, "Aluminophosphate Molecular Sieves and the Periodic Table," Flanigen et al. (Kodansha Ltd., Tokyo, Japan 1986).

Many natural zeolites such as ferrierite, heulandite and stilbite feature a one-dimensional pore structure with a pore size at or slightly smaller than about 0.42 nm diameter. These same zeolites can be converted to zeolites with the desired larger channel sizes by removing the associated alkali metal or alkaline earth metal by methods known in the art, such as ammonium ion exchange, optionally followed by calcination, to yield the zeolite in substantially its hydrogen form. See e.g., U.S. Pat. Nos. 4,795,623 and 4,942,027 incorporated herein by reference. Replacing the associated alkali or alkaline earth metal with the hydrogen form correspondingly enlarges the channel diameter. It is understood that the channel diameter or "size" shall mean the effective channel diameter or size for diffusion.

Alternatively, natural zeolites with too large a channel size, such as some forms of mordenite, can be altered by substituting the alkali metal with larger ions, such as larger alkaline earth metals to reduce the channel size and thus become useful for the processes of this invention.

Particularly preferred zeolites are those having the ferrierite isotypic framework structure (or homeotypic). See the Atlas of Zeolite Structure Types, by W. M. Meier and D. H. Olson, published by Butterworth-Heinemann, third revised edition, 1992, page 98. The prominent structural features of ferrierite found by x-ray crystallography are parallel channels in the alumino-silicate framework which are roughly elliptical in cross-section. Examples of such zeolites having the ferrierite isotypic framework structure include natural and synthetic ferrierite (can be orthorhombic or monoclinic), Sr-D, FU-9 (EP B-55,529), ISI-6 (U.S. Pat. No. 4,578,259), NU-23 (E.P. A-103,981), ZSM-35 (U.S. Pat. No. 4,016,245) and ZSM-38 (U.S. Pat. No. 4,375,573). The hydrogen form of ferrierite (H-ferrierete) is the most preferred zeolite and considered to be substantially one-dimensional, having parallel running channels, with elliptical channels having free diameters of 4.2 Å×5.4 Å along the x and y planes in the [001] view, which is large enough to permit entry of a linear olefin and diffusion out of or through the channel of the methyl branched isoolefin and small enough to retard coke formation. Methods for preparing various H-ferrierite are described in U.S. Pat. Nos. 4,251,499, 4,795,623 and 4,942,027, incorporated herein by reference.

The skeletal isomerization catalyst used in the isomerization processes of this invention may be combined with a refractory oxide that serves as a binder material. Suitable refractory oxides include natural clays, such as bentonite, montmorillonite, attapulgite, and kaolin; alumina; silica; silica-alumina; hydrated alumina; titania; zirconia and mixtures thereof. The weight ratio of zeolite to binder material suitably ranges from about 10:90 to about 99.5:0.5, preferably from about 75:25 to about 99:1, more preferably from about 80:20 to about 98:2 and most preferably from about 85:15 to about 95:5 (anhydrous basis).

Preferably the binder is, for example, the silicas, the aluminas, the silica-aluminas and the clays. More preferred binders are aluminas, such as pseudoboehmite, gamma and bayerite aluminas. These binders are readily available commercially and are used to manufacture alumina-based catalysts. LaRoche Chemicals, through its VERSAL Registered TM family of aluminas and Vista Chemical Company, through its CATAPAL Registered TM aluminas, provide suitable alumina powders which can be used as binders in preparing the instant catalysts. Preferred alumina binders to be used in the preparation of the catalyst, particularly when extrusion is utilized, are the high-dispersity alumina powders. Such high-dispersity aluminas have a dispersity of greater than 50% in a aqueous acid dispersion having an acid content of 0.4 milligram equivalents of acid (acetic) per gram of A1203. Such high-dispersity aluminas are exemplified by Vista's CATAPAL Registered TM D alumina.

Preferably, the skeletal isomerization catalyst is also prepared with at least one acid selected from monocarboxylic acids and inorganic acids and at least one organic acid with at least two carboxylic acid groups ("polycarboxylic acid"). Preferred monocarboxylic acid includes monocarboxylic acid having substituted or unsubstituted hydrocarbyl group having 1 to 20 carbon atoms which can be aliphatic, cyclic or aromatic. Examples include acetic acid, formic acid, propionic acid, butyric acid, caproic acid, glycolic acid, lactic acid, hydroxylbutyric acid, hydroxycyclopentanoic acid, salicylic acid, mandelic acid, benzoic acid, and fatty acids. Preferred inorganic acid includes mineral acids such as nitric acid, phosphoric acid, sulfuric acid and hydrochloric acid.

The preferred polycarboxylic acid is an organic acid with two or more carboxylic acid groups attached through a carbon-carbon bond linkage to an hydrocarbyl segment. The linkage can be at any portion of the hydrocarbyl segment. The polycarboxylic acid preferably has an hydrocarbyl segment from 0 to 10 carbon atoms which can be aliphatic, cyclic or aromatic. The hydrocarbyl segment has 0 carbon atoms for oxalic acid with two carboxylic acid groups attached through the carbon-carbon bond. Examples of the polycarboxylic acids includes, for example, tartaric acid, citric acid, malic acid, oxalic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphtalic acid, dihydroxyfumaric acid, tricarballylic acid, benzene-1,3,5-tricarboxylic acid, isocitric acid, mucic acid and glucaric acid. The polycarboxylic acids can be any isomers of the above acids or any stereoisomers of the above acids. Polycarboxylic acids with at least two carboxylic acid groups and at least one hydroxyl group is more preferred. The most preferred second acids (i.e., polycarboxylic acids) are citric acid, tartaric acid and malic acid.

Optionally, coke oxidation promoting metals can be incorporated into the instant catalysts to promote the oxidation of coke in the presence of oxygen at a temperature greater about 250° C. While the term "metal(s)" is used herein in reference to the oxidation catalysts, these metals will not necessarily be in the zero-valent oxidation state and in many cases will be in the higher oxidation states. Thus, "metal(s)" can encompass the oxides as well as the metals. Preferably the coke oxidation-promoting metal(s) used are transition and rare earth metals. More preferably the coke oxidation-promoting metals are selected from Groups IB, VB, VIB, VIIB and VIII of the transition metal series of the Periodic Table. Specifically preferred are Pd, Pt, Ni, Co, Mn, Ag and Cr. Most preferred are the Group VIII metals palladium and/or platinum. The amount of metal introduced can be up to about 2% by weight, measured as the metal per total weight of the catalyst. When using platinum and/or palladium, smaller amounts of metals rather than larger amounts of metals incorporated into the zeolite/binder are preferred. Preferably platinum and/or palladium will range from about 5 ppm to about 3000 ppm by weight, basis metal, of the final catalyst.

In a preferred method, the instant catalysts can be prepared by mixing a mixture of at least one zeolite as herein defined, alumina-containing binder, water, at least one monocarboxylic acid or inorganic acid and at least one polycarboxylic acid in a vessel or a container, forming a pellet of the mixed mixture and calcining the pellets at elevated temperatures. In one preferred embodiment zeolite powder and alumina-containing powder is mixed with water and one or more of monocarboxylic acid or inorganic acid (first acid) and one or more of polycarboxylic acid (second acid) and optionally one or more compounds of the coke-oxidation promoting metal and the resulting mixture (paste) is formed into a pellet. The coke-oxidation promoting metal may alternatively be impregnated.

Preferably the pellet is formed by extrusion but can also be formed into catalytically useful shape by pressing hydrostatically or mechanically by pressing into die or mold. When extrusion is used optional extrusion aids such as cellulose derivatives, e.g., METHOCEL Registered TM F4M hydroxypropyl methylcellulose, can be utilized (manufactured by The Dow Chemical Company). The term "pellets" as used herein can be in any shape or form as long as the materials are consolidated. The formed pellets are calcined at a temperature ranging from a lower range of from about 200° C., preferably from about 300° C., more preferably from about 450° C., to an upper range of up to about 700° C., preferably up to about 600° C., more preferably up to about 525° C.

The ratio of the first acids to second acids is preferably within the range of about 1:60 to about 60:1, more preferably 1:10 to about 10:1. The amount of the first acid used is in an amount effective to peptize the mixture. Preferably the amount of the first acid used is from about 0.1 weight percent to about 6 weight percent, more preferably from about 0.5 weight percent to about 4 weight percent based on the combined weight of zeolite and alumina-containing binder (anhydrous solids basis). Aluminas with lower dispersibilities than Vista Catapal D may require greater amounts of acid to peptize them. The amount of the second acid used is in an amount effective to promote the catalytic activity of the catalyst which is from about 0.1 weight percent to about 6 weight percent, preferably from about 0.2 weight percent to about 4 weight percent based on the combined weight of zeolite and alumina-containing binder (anhydrous solids basis).

The mixture is mixed thoroughly or vigorously until the mixture appears uniform. The mixing can be performed by combining all of the components of the mixture at once or by adding the components of the mixture at different stages of mixing. The mixing can be accomplished by mulling. The term "mulling" is used herein to mean mixing of powders to which sufficient water has been added to form a thick paste and wherein the mixing is accompanied by shearing of the paste. Commercially available mullers such as the Lancaster Mix Muller and the Simpson Mix Muller can be used to carry out the mixing. A commercial blender such as a ribbon blender and/or a powder mill can also be used to carry out the mixing.

Optionally the coke-oxidation promoting metal can be impregnated to the formed pellet with a metals-containing solution instead of mixing in the paste mixture. The skeletally isomerized olefins are subsequently converted to any of a broad range of surfactants, including nonionic, anionic, cationic, and amphoteric surfactants. The skeletally isomerized olefin serves as a surfactant intermediate. Specifically, the skeletally isomerized olefin serves as the hydrophobic moiety of the surfactant molecule, while the moiety added to the olefin during the conversion process serving as the hydrophile. Neither the particular surfactant nor the means used to convert the skeletally isomerized olefin to an alcohol or surfactant is considered critical to the present invention, provided that it does not rearrange the skeletal structure of the olefin to the extent that the byproduct is no longer biodegradable, or reduces the degree of branching to less than 1.5.

The temperature at which the isomerization may be conducted may range from 200° C. to 500° C. Temperatures should not exceed the temparture at which the olefin will crack. Suitable pressures maintained during the isomerization reaction is at an olefin partial pressure ranging from 0.1 atmospheres to 10 atmospheres, more preferably from above ½ atmosphere to 5 atmospheres, most preferably above ½ to 2 atmospheres.

Conversion of the skeletally isomerized olefins to a primary alcohol composition is conveniently accomplished, for example, by hydroformylation, by oxidation and hydrolysis, by sulfation and hydration, by epoxidations and hydration, or the like. In hydroformylation, the skeletally isomerized olefins are converted to alkanols by reaction with carbon monoxide and hydrogen according to the Oxo process. Most commonly used is the "modified Oxo process", using a phosphine, phosphite, arsine or pyridine ligand modified cobalt or rhodium catalyst, as described in U.S. Pat. Nos. 3,231,621; 3,239,566; 3,239,569; 3,239,570; 3,239,571; 3,420,898; 3,440,291; 3,448,158; 3,448,157; 3,496,203; and 3,496,204; 3,501,515; and 3,527,818, the disclosures of which are incorporated herein by reference. Methods of production are also described in Kirk Othmer, "Encyclopedia of Chemical Technology" $3^{rd}$ Ed. vol 16, pages 637–653; "Monohydric Alcohols: Manufacture, Applications and Chemistry", E. J. Wickson, Ed. Am. Chem. Soc. 1981, incorporated herein by reference.

Hydroformylation is a term used in the art to denote the reaction of an olefin with CO and $H_2$ to produce an aldehyde/alcohol which has one more carbon atom then the reactant olefin. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative catalysts include cobalt hydrocarbonyl catalyst, cobalt-phosphine ligand catalyst, and rhodium-phosphine ligand catalyst. The choice of catalysts determines the various reaction conditions imposed. These conditions can vary widely, depending upon the particular catalysts. For example, temperatures can range from about room temperatures to about 300° C. When cobalt carbonyl catalysts are used, which are also the ones typically used, temperatures will range from about 150° to about 250° C. One of ordinary skill in the art, by referring to the above-cited references, or any of the well-known literature on oxo alcohols can readily determine those conditions of temperature and pressure that will be needed to hydroformylate the dimerized olefins.

Tyical reaction conditions, however, can be suitably carried out at moderate conditions. Temperatures in the range of 125° C. to 200° C. are recommended. Reaction pressures in the range of about 300 psig to about 1500 psig are typical, but lower or higher pressures may be selected. Ratios of catalyst to olefin ranging from 1:1000 to 1:1 are suitable. The ratio of hydrogen to carbon monoxide can vary widely, but is usually in the range of 1 to about 10, preferably from about 2 moles of hydrogen to one mole of carbon monoxide to favor the alcohol product.

The hydroformylation process can be carried out in the presence of an inert solvent, although it is not necessary. A variety of solvents can be applied such as ketones, e.g. acetone, methyl ethyl ketone, methyl isobutyl ketone, acetophenone and cyclohexanone; aromatic compounds such as benzene, toluene and the xylenes; halogenated aromatic compounds such as chlorobenzene and orthodichlorobenzene; halogenated paraffinic hydrocarbons such as methylene chloride and carbon tetrachloride; paraffins such as hexane, heptane, methylcyclohexane and isooctane and nitriles such as benzonitrile and acetonitrile.

With respect to the catalyst ligand, mention may be made of tertiary organo phosphines, such as trialkyl phosphines, triamyl phosphine, trihexyl phosphine, dimethyl ethyl phosphine, diamylethyl phosphine, tricyclopentyl(or hexyl) phosphine, diphenyl butyl phosphine, dipenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines. Included as bidentate-type ligands are tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands are the phosphabicyclohydrocarbons, such as 9-hydrocarbyl-9-phosphabicyclononane in which the smallest P-contianing ring contains at least 5 carbon atoms. Some examples include 9-aryl -9-phosphabicyclo[4.2.1]nonane, (di)alkyl-9-aryl -9-phosphabicyclo[4.2.1]nonane, 9-alkyl -9-phosphabicyclo[4.2.1]nonane, 9-cycloalkyl -9-phosphabicyclo[4.2.1]nonane, 9-cycloalkenyl -9-phosphabicyclo [4.2.1]nonane, and their [3.3.1] and [3.2.1] counterparts, as well as their triene counterparts.

The branched primary alcohol composition of the invention is suitable for the manufacture of anionic, nonionic, and cationic surfactants, preferably the former two, more preferably the anionic. Specifically, the branched primary alcohol composition of the invention can be used as the pecursor for the manufacture of anionic sulfates, including alcohol sulfates and oxylakylated alcohol sulfates, and nonionic oxyalkylated alcohols.

Any technique known for sulfating alcohols can be used herein. The primary alcohol composition may be directly sulfated, or first oxyalkylated followed by sulfatation. A preferred class of compositions comprises at least one anionic surfactant comprising the condensation product of the C8 to C36, particularly the C11 to C19 skeletally isomerized primary alcohol composition with or without ethylene oxide and/or propylene oxide, in which the number of ethoxy groups ranges from 3 to 12 and the ratio ethoxy/propoxy is from 4 to 12, followed by sulfation.

The general class of anionic surfactants or alcohol ethoxysulfates can be characterized by the chemical formula:

$$R'\text{—}O\text{—}(CH_2\text{—}CH_2\text{—}O)_x\text{—}SO_3M \quad (II)$$

wherein R' represents the skeletally isomerized olefin hydrophobe moiety, x represents the average number of oxyethylene groups per molecule and is in the range of from about 0 to about 12, and M is a cation selected from an alkali metal ion, an ammonium ion, and mixtures thereof. Of course, the surfactant can by oxyalkylated with any oxirane containing compound other than, in mixture with, or sequentially with ethylene oxide.

Sulfonation processes are described, for instance, in U.S. Pat. No. 3,462,525, issued Aug. 19, 1969 to Levinsky et. al., U.S. Pat. No. 3,428,654 issued Feb. 18, 1969 to Rubinfeld et. al., U.S. Pat. No. 3,420,875 issued Jan. 7, 1969 to DiSalvo et. al., U.S. Pat. No. 3,506,580 issued Apr. 14, 1970 to Rubinfeld et. al., U.S. Pat. No. 3,579,537 issued May 18, 1971 to Rubinfeld et. al., and U.S. Pat. No. 3,524,864 issued Aug. 18, 1970 to Rubinfeld, each incorporated herein by reference. Suitable sulfation procedures include sulfur trioxide (SO3) sulfation, chlorosulfonic acid (ClSO3H) sulfation and sulfamic acid (NH2SO3H) sulfation. When concentrated sulfuric acid is used to sulfate alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 mole to about 1.3 moles of sulfuric acid per mole alcohol, preferably from about 0.4 mole to about 1.0 mole of sulfuric acid per mole of alcohol.

A typical sulfur trioxide sulfation procedure includes contacting liquid alcohol or its ethoxylate and gaseous sulfur trioxide at about atmospheric pressure in the reaction zone of a falling film sulfator cooled by water at a temperature in the range of from about 25° C. to about 70° C. to yield the sulfuric acid ester of alcohol or its ethoxylate. The sulfuric acid ester of the alcohol or its ethoxylate then exits the falling film column and is neutralized with an alkali metal solution, e.g., sodium or potassium hydroxide, to form the alcohol sulfate salt or the alcohol ethoxysulfate salt.

Suitable oxyalkylated alcohols can be prepared by adding to the alcohol or mixture of alcohols to be oxyalkylated a calculated amount, e.g., from about 0.1 percent by weight to about 0.6 percent by weight, preferably from about 0.1 percent by weight to about 0.4 percent by weight, based on total alcohol, of a strong base, typically an alkali metal or alkaline earth metal hydroxide such as sodium hydroxide or potassium hydroxide, which serves as a catalyst for oxylalkylation. The resulting mixture is dried, as by vapor phase removal of any water present, and an amount of alkylene oxide calculated to provide from about 1 mole to about 12 moles of alkylene oxide per mole of alcohol is then introduced and the resulting mixture is allowed to react until the alkylene oxide is consumed, the course of the reaction being followed by the decrease in reaction pressure.

The oxyalkylation is typically conducted at elevated temperatures and pressures. Suitable reaction temperatures range from about 120° C. to about 220° C. with the range of from about 140° C. to about 160° C. being preferred. A suitable reaction pressure is achieved by introducing to the reaction vessel the required amount of alkylene oxide which has a high vapor pressure at the desired reaction temperature. For consideration of process safety, the partial pressure of the alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkyelene oxide if suitable precautions, known to the art, are taken to manage the risks of explosion. With respect to ethylene oxide, a total pressure of between about 40 and 110 psig, with an ethylene oxide partial pressure between about 15 and 60 psig, is particularly preferred, while a total pressure of between about 50 and 90 psig, with an ethylene oxide partial pressure between about 20 and 50 psig, is considered more preferred. The pressure serves as a measure of the degree of the reaction and the reaction is considered to be substantially complete when the pressure no longer decreases with time.

It should be understood that the oxyalkylation procedure serves to introduce a desired average number of alkylene oxide units per mole of alcohol oxyalkylate. For example, treatment of an alcohol mixture with 3 moles of ethylene oxide per mole of alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3. In a typical ethoxylation product mixture, there is also a minor proportion of unreacted alcohol.

Other alkyene oxides can be used, such a proplyene oxide and butylene oxide. These may be added as a heteric mixture to the alcohol or sequentially to make a block stucture.

The sulfated primary alcohol composition of the invention can be used as surfactants in a wide variety of applications, including detergents such as granular laundry detergents, liquid laundry detergents, liquid dishwashing detergents; and in miscellaneous formulations such as general purpose cleaning agents, liquid soaps, shampoos and liquid scouring agents.

The sulfated primary alcohol composition of the invention find particular use in detergents, specifically laundry detergents. These are generally comprised of a number of components, besides the sulfated primary alcohol composition of the invention:

other surfactants of the ionic, nonionic, amphoteric or cationic type, builders (phosphates, zeolites),cobuilders (polycarboxylates), bleaching agents and their activators, foam controlling agents, enzymes, anti-greying agents, optical brighteners, and stabilizers.

Liquid laundry detergents generally comprise the same components as granular laundry detergents, but generally contain less of the inorganic builder component. Hydrotropes are often present in the liquid detergent formulations. General purpose cleaning agents may comprise other surfactants, builders, foam suppressing agents, hydrotropes and solubilizer alcohols.

In addition to surfactants, washing and cleaning agents may contain a large amount of builder salts in amounts up to 90% by weight, preferably between about 5 and 35% by weight, to intensify the cleaning action. Examples of common inorganic builders are phosphates, polyphosphates, alkali metal carbonates, silicates and sulfates. Examples of organic builders are polycarboxylates, aminocarboxylates such as ethylenediaminotetraacetates, nitrilotriacetates, hydroxycarboxylates, citrates, succinates and substituted and unsubstituted alkanedi- and polycarboxylic acids. Another type of builder, useful in granular laundry and built liquid laundry agents, includes various substantially water-insoluble materials which are capable of reducing the water hardness e.g. by ion exchange processes. In particular the complex sodium aluminosilicates, known as type A zeolites, are very useful for this purpose.

The formulations may also contain percompounds with a bleaching action, such as perborates, percarbonates, persulfates and organic peroxy acids. Formulations containing percompounds may also contain stabilizing agents, such as magnesium silicate, sodium ethylenediaminetetraacetate or sodium salts of phosphonic acids. In addition, bleach activators can be used to increase the efficiency of the inorganic persalts at lower washing temperatures. Particularly useful for this purpose are substituted carboxylic acid amides, e.g., tetraacetylethylenediamine, substituted carboxylic acids, e.g., isononyloxybenzenesulfonate and sodiumcyanamide.

Examples of suitable hydrotropic substances are alkali metal salts of benzene, toluene and xylene sulfonic acids; alkali metal salts of formic acid, citric and succinic acid, alkali metal chlorides, urea, mono-, di-, and triethanolamine. Example of solubilizer alcohols are ethanol, isopropanol, mono- or polyethylene glycols, monoproylene glycol and etheralcohols.

Examples of foam control are high molecular weight fatty acid soaps, paraffinic hydrocarbons, and silicon containing defoamers. In particular hydrophobic silica particles are efficient foam control agents in these laundry detergent formulations.

Examples of known enzymes which are effective in laundry detergent agents are protease, amylase and lipase. Preference is given to the enzymes which have their optimum performance at the design conditions of the washing and cleaning agent.

A large number of fluorescent whiteners are described in the literature. For laundry washing formulations, the derivatives of diaminostilbene disulfonates and substituted distyrylbiphenyl are particularly suitable.

As antigreying agents, water soluble colloids of an organic nature are preferably used. Examples are water soluble polyanionic polymers such as polymers and copolymers of acrylic and maleic acid, cellulose derivatives such as carboxymethyl cellulose methyl- and hydroxyethylcellulose.

In addition to one or more of the aforementioned other surfactants and other detergent composition components, compositions according to the invention typically comprise one or more inert components. For instance, the balance of liquid detergent composition is typically an inert solvent or diluent, most commonly water. Powdered or granular detergent compositions typically contain quantities of inert filler or carrier materials.

The following examples will illustrate the nature of the invention without its scope.

EXAMPLE 1

This example will demonstrate the manufacture of a skeletally isomerized $C_{16}$ olefin, subsequently converted to a skeletally isomerized $C_{17}$ primary alcohol composition according to the invention.

About 1 liter of NEODENE® 16 olefin, a $C_{16}$ linear α-olefin commercially available from Shell Chemical Company, was first dried and purified through alumina. The olefin was then passed through a tube furnace at about 250° C. set at a feed rate of about 1.0 ml/minute and using a nitrogen pad flowing at about 91 cc/minute. Working from the top, the tube furnace was loaded with glass wool, then about 10 ml of silicon carbide, then the catalyst, followed by 5 ml of silicon carbide, and more glass wool at the bottom. The volume of the tube furnace was about 66 ml. The reactor tube furnace had three temperature zones, with a multipoint thermocouple inserted into the tube reactor and positioned such that the temperature above, below and at three different places in the catalyst bed could be monitored. The reactor was inverted and installed the in the furnace. All three zones, including the catalyst zone, were kept at about 250° C. during the reaction and the pressure was maintained in the reactor at about 2 psig.

The amount of catalyst used was about 23.1 g, or about 53 ml by volume. The type of catalyst used to structurally isomerize the NEODENE® 16 olefin was a $\frac{1}{16}$" extruded and calcined H-ferrierite containing 100 ppm palladium metal.

This catalyst was prepared in accordance with example C of U.S. Pat. No. 5,510,306, reproduced in part herein for convenience. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite. The catalyst components were mulled using a Lancaster mix muller. The mulled catalyst material was extruded using an 1 inch or a 2.25 inch Bonnot pin barrel extruder.

The catalyst was prepared using 1weight percent acetic acid and 1 weight percent citric acid. The Lancaster mix muller was loaded with 645 grams of ammonium-ferrierite (5.4% LOI) and 91 grams of CATAPAL Registered TM D alumina (LOI of 25.7%). The alumina was blended with the ferrierite for 5 minutes during which time 152 milliliters of de-ionized water was added. A mixture of 6.8 grams glacial acetic acid, 7.0 grams of citric acid and 152 milliliters of de-ionized water was added slowly to the muller in order to peptize the alumina. The mixture was mulled for 10 minutes. 0.20 Grams of tetraammine palladium nitrate in 153 grams of de-ionized water were then added slowly as the mixture was mulled for a period of 5 additional minutes. Ten grams of METHOCEL Registered TM ®F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a die plate with $\frac{1}{8}$" holes.

The moist extrudates were tray dried in an oven heated to 150° C. 2 hours, and then increased to 175° C. for 4 hours. After drying, the extrudates were longsbroken manually. The extrudates were calcined in flowing air at 500° C. for two hours.

The olefin was passed through the reactor furnace over a 5 hour period. Samples of 36.99 g and 185.38 g were collected at about the 1 and 5 hour point, and combined for a total of about 222 g. A portion of this sample was then vacuum distilled at about 4 mmHg to obtain a predominate amount of the $C_{16}$ skeletally isomerized olefin by collecting distillate cuts boiling at 160° C. in the pot and 85° C. at the head, and 182° C. in the pot and 75° C. at the head.

A 90 gram sample of the 110.93 grams of the skeletally isomerized olefin was then hydroformlyated using the modified oxo process. 90 grams of the skeletally isomerized olefin was reacted with hydrogen and carbon monoxide in about a 1.7:1 molar ratio in the presence of a phosphine modified cobalt catalyst at a temperature of up to about 185° C. and a pressure of about 1100 psig for about four and one-half hours in a nitrogen purged 300 cc autoclave. After completion of the reaction, the product was cooled to 60° C.

About 40 grams of the hydroformylated product was poured into a 100 ml flask and vacuum distilled for about 4 hours at about 4 mmHg with temperature increases from start of 89° C. to a finish temperature of 165° C. Distillate cuts of 20.14 g and 4.12 g were taken at 155° C. and 165° C., respectively, and combined in a 100 ml flask.

To the distillate cuts in the flask was added 0.2 g of sodium borohydride, stirred, and heated up to 90° C. over an 8 hour period to deactivate the hydroformylation catalyst and stabilize the alcohols. The distilled alcohol was washed with 90° C. water three times, dried with sodium sulfate, and filtered into a 100 ml flask. The alcohol was then vacuum distilled for about 1 more hour to distill off any remaining water. The product was then subjected to NMR analysis and sulfation to test for cold water solubility, detergency, and biodegradability.

EXAMPLE 2

This example will demonstrate the manufacture of a skeletally isomerized $C_{13-14}$ olefin, subsequently converted to a skeletally isomerized $C_{14-15}$ primary alcohol composition according to the invention.

A composition of a $C_{13-14}$ internal olefin was subjected to skeletal isomerization using the same procedure and type of equipment as described above in example 1. The olefin was passed through the tube furnace for about 26 hours, except that after about 8 hours the temperature of the tube furnace was increased in all three zones to about 275° C. At about the 13 hour, 18 hour, 20 hour, and 26 hour mark, samples of the skeletally isomerized olefins were collected and combined for a total of about 774 g. The skeletally isomerized olefin was then vacuum distilled at about 4 mmHg. About 636 g of distillate boiling in the pot at temperatures in the range of 135° C. to 145° C. and at the head within the range of 108° C. to 138° C. were collected.

About 606 g of the skeletally isomerized distilled olefin was hydroformylated by the above procedure, except in a 1 gallon autoclave using a 37/63 mole % ratio of carbon monoxide to hydrogen for a period of about 12–13 hours at about 700 to 800 psig and 175° C. About 693 g of alcohol was collected.

The alcohol was then flash distilled at 4 mmHg to collect the $C_{14-15}$ alcohol, with about 650 g of distillate cut boiling in pot at 185° C. and at the head at 140° C. collected. This cut was treated with 5.0 g of sodium borohydride, heated to about 100° C., and then treated with 5.0 more grams of sodium borohydride, for a total heat time of about 9 hours. The alcohol was washed with 90° C. water three times, dried with sodium sulfate, filtered, and vacuum distilled at 4 mmHg. Distillate cuts boiling at 128° C. through 142° C. at the head were collected and tested with NMR, after which they were sulfated and tested for cold water solubility, detergency, and biodegradability.

EXAMPLE 3

The same procedure as used in example 1 was used to skeletally isomerize a NEODENE® 14 olefin commercially available from Shell Chemical Company, which is a $C_{14}\alpha$- olefin, with subsequent conversion to a skeletally isomerized $C_{15}$ primary alcohol composition. The tube furnace was kept at about 250° C. The skeletally isomerized distillate cut boiling at 133° C. in the pot and 64° C. at the head was collected and hydroformylated at 1300–1400 psig for 5 hours at a molar ratio of $H_2$/CO of 1.7:1, using the equipment in example 1.

EXAMPLE 4

The same procedure as used in example 1 was employed to skeletally isomerize a NEODENE® 12 olefin, a $C_{12}\alpha$-olefin, subsequently converted to a skeletally isomerized $C_{13}$ primary alcohol composition. The skeletally isomerized olefin was vacuum distilled at 20 mmHg, and the distillate cut boiling at 172° C. in the pot and 105° C. at the head was collected and hydroformylated to an alcohol. The hydroformylation equipment was as used in example 2, at about 1165 psig over an 8 hour period, using a 37/63 mole % CO/H gas mixture. The alcohol was vacuum distilled at 10 mmHg, with those cuts boiling at 141°–152° C. in the pot and 127°–132° C. at the head being collected.

EXAMPLE 5

The same olefin, procedure, and type of equipment as used in example 2 was repeated. The $C_{13-14}$ internal olefin was skeletally isomerized at 250° C. The isomerized olefin was vacuum distilled at 4 mmHg, with distillate cuts boiling at 95° C. and, 77° C. at the head being collected, as well as distillate cuts boiling between 120° C. to 175° C. in the pot and 73° C. to 106° C. at the head being collected under 20 mmHg. The hydroformylation was conducted in an autoclave for about 9 hours at a pressure of about 1165 psig using a CO to H gas ratio of 37/63 mole %. Afterwards, the distillate cut boiling at 173° C. in the pot and 125° C. at the head was collected and treated with sodium borohydride as in example 2.

EXAMPLE 6

Each of the primary alcohol compositions described in examples 1–6 were sulfated by adding dropwise chlorosulfonic acid to the primary alcohol composition. Specifically, the primary alcohol composition was sparged for 2–3 hours with nitrogen in a flask, after which about 1 ml of methylene chloride per gram of the primary alcohol composition was added. The chlorosuflonic acid was added dropwise to the primary alcohol composition in the flask for about 25 minutes, while maintaining the temperature at about 30°–35° C. More methylene chloride was added if the solution became to viscous. The solution was then sparged with nitrogen for 2–3 minutes to facilitated removal of HCl, after which it was added slowly to a chilled 50% sodium hydroxide in 3A alcohol solution to neutralize the primary alcohol composition. If the pH was below 8, more of the basic solution was added, until the pH was adjusted to between 8–9. If too acidic, a 50% solution of $H_2SO_4$ was added to adjust the pH. The solution was stirred for another hour, and the pH adjusted accordingly within the stated range. Methylene chloride was removed by a rotary evaporator under reduced pressure at about 40° C. under a nitrogen sparge.

The primary alcohol compositions were subsequently tested for amount, type, and location of branching using the JSME NMR method described herein. For a determination of quaternary carbon atoms, the quat only JSME NMR technique described herein was used. These results are reported in Table 1 below. The sulfated primary alcohol samples were also tested for biodegradability, the results of which are reported in Table II; and detergency, the results of which are reported in Table III. The examples reported in the tables are arranged by order of chain length for ease of viewing, and identified as 6- indicating the sulfate of a corresponding example number. Each of these tests were conducted in accordance with the procedures specified above. As a comparison example, Neodol® 45-S was tested for branching, biodegradability, and detergency. Neodol® 45-S was used as the comparison because it is the current commercial primary alcohol composition, which when sulfated, is currently used in detergents and is known for its ready biodegradability.

TABLE I

NMR Structural Characterization

| Analysis | Ex 4, a $C_{13}$ alcohol | Ex 2, a $C_{14-15}$ alcohol | Ex 3, a $C_{15}$ alcohol | Ex 1, a $C_{17}$ alcohol | Neodol ® 45, a $C_{14-15}$ alcohol |
|---|---|---|---|---|---|
| Average Carbon Number | 13.9 | 15.1 | 15.0 | 17.0 | 14.7 |
| Average Branches per Chain | 1.3 | 1.6 | 1.3 | 1.6 | 0.3 |
| Branch Position Relative To Hydroxyl Carbon | | | | | |
| % @ C4 position and further, including no branching | 70.2 | 67.1 | 65.1 | 67.9 | 81.5 |
| % @ C3 position | 20.6 | 20.5 | 19.6 | 21.0 | 0.0 |
| % methyl @ C2 position | 4.7 | 5.9 | 5.2 | 4.0 | 7.4 |
| % ethyl @ C2 position | 1.0 | 1.3 | 2.3 | 1.2 | 2.7 |
| % propyl and longer @ C2 position | 3.5 | 5.3 | 7.8 | 5.9 | 8.4 |
| Types Of Branching | | | | | |
| % Propyl and longer | 38 | 32.5 | 37.6 | 41.7 | 88.8 |
| % ethyl | 10.8 | 12.5 | 12.8 | 16.3 | 3.1 |
| % methyl | 38.2 | 38.9 | 38.3 | 42.0 | 8.1 |
| % isopropyl termination | 13.0 | 16.1 | 11.3 | 0.0 | 0.0 |
| % Linear Alcohol (By GC) | na | <2% | na | <1% | 78% |
| Quaternary Carbons Detected | none | none | not analyzed | none | none |

The results above indicate that the skeletally isomerized branched alcohols have a very high average number of branches per molecule chain, well exceeding 0.7, while the commercial Neodol® 45, sulfated, has an average number of branches which is quite low, on the order of 0.3. The patterns of branching are strikingly similar for the different alcohols, except that the branched $C_{17}$ is curiously deficient in isopropyl termination. The results also indicate a sharp increase in the number of branches occurring at the $C_3$ position compared to the lack of any branches in the Neodol 45 alcohol at the $C_3$ position. Of the types of branches detected, most of the branches are methyl groups for both the skeletally isomerized alcohols and the linear Neodol® alcohol. However, the skeletally isomerized alcohol methyl branches are not concentrated at the $C_2$ position, as is the case for Neodol 45 and conventional Neodols. A further distinguishing feature of the skeletally isomerized alcohols is that they contain a larger proportion of ethyl types of branches than the Neodol 45. Further, except the $C_{17}$ alcohol, most of the embodiments were also skeletally isomerized at the terminal part of the hydrophobe, as indicated by the high percentage of terminal isopropyl formation, in contrast to none found in the Neodol 45.

The results also support a conclusions that a predominate number of branches in the skeletally isomerized alcohols are concentrated towards the ends of the molecule chain, i.e., at the $C_2$, $C_3$, and at the isopropyl terminal position, rather than towards the center of the molecule chain. NMR data showing a high percentage of methyl, ethyl, and isopropyl branching for a compound whose branching is predominately towards the center of the chain, i.e. inward from the fourth carbon on either end of the chain, typically have very low percentages of branching at the $C_2$ and $C_3$ positions. The data above, however, shows both a high percentage of methyl, ethyl, and isopropyl types of branches as well as a high amount of branching occurring at the $C_2$ and $C_3$ positions, indicating that the molecule has a higher concentration of branches at the $C_2$ and $C_3$ carbon positions at the ends of the carbon molecule than the number of branches found at the $C_4$ or longer positions from both ends of the molecule proceeding inward towards the center.

Finally, in spite of the high number of branches per molecule chain, no quaternary carbon atoms were detected by the modified NMR JSME method. This would suggest that these compounds should readily biodegrade.

TABLE II

% Biodegradation of Skeletally Isomerized Alcohol Sulfates

| Example No. | 5-day | 10-day | 15-day | 28-day |
|---|---|---|---|---|
| 6-4, a $C_{13}$ alcohol sulfate | 47 | 61 | 71 | 100 |
| 6-2, a $C_{14-15}$ alcohol sulfate | 38 | 58 | 65 | 100 |
| 6-3, a $C_{15}$ alcohol sulfate | 22 | 48 | 63 | 69 |
| 6-1, a $C_{17}$ alcohol sulfate | 44 | 56 | 70 | 89 |
| A sulfated Neodol ® $C_{14-15}$ alcohol | 44 | 63 | 78 | 86 |

The OECD 301D biodegradation results indicate that each of the sulfated primary alcohol compositions of the invention readily biodegraded. Some of the sulfated primary alcohol compositions of the invention even exhibited 100% biodegradation at 28 days.

TABLE III

Multisebum Detergencies of Skeletally Isomerized Alcohol Sulfates

| Example No. | 50° F. | 90° F. |
|---|---|---|
| 6-4, a $C_{13}$ alcohol sulfate | 12 | 14 |
| 6-2, a $C_{14-15}$ alcohol sulfate | 37 | 49 |
| 6-3, a $C_{15}$ alcohol sulfate | 39 | 50 |
| 6-1, a $C_{17}$ alcohol sulfate | 24 | 35 |
| A sulfated Neodol ® $C_{14-15}$ alcohol | 16 | 34 |

$LSD_{95}$ is 5.0 at both temperatures.

The detergency results indicate that the alcohol sulfate compositions of the invention exhibited extremely good cold water detergency. For example, 6–2 far outperformed the sulfated Neodol® alcohol, each of equal chain length, in both cold and warm water detergency. A composition having good cold water detergency is one in which has superior cold water detergency over a sulfated Neodol® alcohol of the same chain length. Preferred, however, are those alcohol sulfates which have a cold water detergency of 22% or more, most preferably 28% or more.

What we claim is:

1. A branched primary alcohol composition having 8 to 36 carbon atoms, an average number of branches per molecule chain of at least 0.7, less than 0.5 atom % of quaternary carbon atoms, said branching comprising methyl and ethyl branching.

2. The alcohol composition of claim 1, wherein wherein the average number of branches per chain ranges from 1.5 to 2.3.

3. The alcohol composition of claim 2, wherein said alcohol composition contains less than 5% linear alcohols.

4. The alcohol composition of claim 3, wherein said alcohol composition contains less than 3% linear alcohols.

5. The alcohol composition of claim 2, wherein from 5–25% of the number of branches are on the $C_2$ atoms of the alcohol composition.

6. The alcohol composition of claim 5, wherein from 10–20% of the number of branches are on the $C_2$ atoms of the alcohol composition.

7. The alcohol composition of claim 2, wherein from 10–50% of the number of branches are on the $C_3$ atoms of the alcohol composition.

8. The alcohol composition of claim 7, wherein from 15–30% of the number of branches are on the $C_3$ atoms of the alcohol composition.

9. The alcohol composition of claim 2, wherein at least 40% of the branches in the alcohol are methyl branches.

10. The alcohol composition of claim 9, wherein at least 50% of the branches are methyl branches.

11. The alcohol composition of claim 1, wherein 5% to 30% of the branches are ethyl branches.

12. The alcohol composition of claim 11, wherein from 10% to 20% of the branches are ethyl branches.

13. A branched primary alcohol composition comprising skeletally isomerized olefins converted to primary alcohols having an average carbon number ranging from 8 to 36 carbon atoms and an average number of branches per molecule ranging from 0.7 to 2.1.

14. The alcohol composition of claim 13, wherein the composition comprises at least 75 wt. % of alcohol molecules having from 11 to 19 carbon atoms.

15. The alcohol composition of claim 13, wherein the average number of branches per alcohol chain is at least 0.7.

16. The alcohol composition of claim 15, wherein the average number of branches per alcohol chain ranges is at least 1.5.

17. The alcohol composition of claim 16, wherein said composition comprises from 5% to 30% ethyl branching.

18. The alcohol composition of claim 13, wherein the skeletally isomerized olefins comprise isopropyl termination types of branches in an amount of at least 5%.

19. The alcohol composition of claim 13, wherein the composition comprises ethyl branching.

20. The alcohol composition of claim 19, comprising from 5% to 30% ethyl branching.

21. The alcohol composition of claim 16, wherein the composition comprises branching at the $C_3$ position of the olefins in an amount of 5% to 30%.

22. The alcohol composition of claim 16, wherein the branches comprise methyl branches numbering at least 40% of the overall branching.

23. The alcohol composition of claim 13, wherein the branches comprise from 5% to 30% ethyl branches.

24. A process for making a branched primary alcohol composition, comprising:
 a) contacting underskeletal isomerization conditions an olefin feed comprising linear olefins having at least 7 carbon atoms with a catalyst effective for skeletally isomerizing said linear olefin to yield a skeletally isomerized olefins; and
 b) converting said skeletally isomerized olefin to said primary alcohol composition.

25. The process of claim 24, wherein said primary alcohol composition comprises has an average number of branches per alcohol chain of at least 1.5.

26. The process of claim 25, wherein said conversion comprises a hydroformylating the skeletally isomerized olefin.

27. The process of claim 24, wherein said catalyst comprises a molecular sieve having at least one channel with a crystallographic free diameter along the x and/or y planes of the [001] view ranging from greater than 4.2 Å and less than 7 Å, and said conversion is by hydroformylation.

28. The process of claim 27, wherein said catalyst comprises a zeolite having a ferrierite isotypic structure.

29. The process of claim 28, wherein said catalyst comprises an H-ferrierite.

30. The process of claim 27, wherein the catalyst has an elliptical pore size large enough to permit entry of a linear olefin and diffusion of a methyl branched isoolefin and small enough to retard coke formation.

31. The process of claim 30, wherein the catalyst is combined with an alumina-containing binder.

32. The process of claim 31, wherein the catalyst is further combined with an acid comprising a monocarboxylic acid, an inorganic acid, or mixtures thereof.

33. The process of claim 11, wherein said olefin feed is contacted with said catalyst at a temperature ranging from 200° C. to the lesser of 500° C. or the temperature at which the olefin cracks.

34. The process of claim 11, wherein said olefin feed is contacted with said catalyst at an olefin partial pressure ranging from 0.1 atmospheres to 10 atmospheres.

35. The process of claim 20, wherein said partial pressure ranges from above 0.5 atmospheres to 2 atmospheres.

36. The process of claim 21, wherein the temperature at which said olefin feed contacts said catalyst ranges from 200° C. to the lesser of 500° C. or the temperature at which the olefin cracks.

37. The process of claim 11, wherein said olefin feed contains greater than 50 percent of linear olefins having an average carbon number ranging from $C_{11}$ to $C_{19}$.

38. The process of claim 17, wherein the olefin feed containing more than 50 percent linear alcohols is converted to skeletally isomerized olefins, and subsequently converted to a primary alcohol composition, wherein less than 5 percent of the alcohol molecules in the primary alcohol composition are linear alcohols.

39. The process of claim 38, wherein less than 3 percent of the alcohol molecules in the primary alcohol composition are linear alcohols.

* * * * *